US009445778B2

(12) United States Patent
Gagnon et al.

(10) Patent No.: US 9,445,778 B2
(45) Date of Patent: Sep. 20, 2016

(54) ECG-GATED TEMPORAL SAMPLING IN CARDIAC KINETIC MODELING

(75) Inventors: Daniel Gagnon, Twinsburg, OH (US); Henning Braess, Uttenreuth (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2822 days.

(21) Appl. No.: 11/912,678

(22) PCT Filed: Apr. 10, 2006

(86) PCT No.: PCT/IB2006/051092
§ 371 (c)(1),
(2), (4) Date: Oct. 5, 2009

(87) PCT Pub. No.: WO2006/114717
PCT Pub. Date: Nov. 2, 2006

(65) Prior Publication Data
US 2010/0016715 A1 Jan. 21, 2010

Related U.S. Application Data

(60) Provisional application No. 60/675,187, filed on Apr. 27, 2005.

(51) Int. Cl.
*A61B 6/00* (2006.01)
*A61B 6/03* (2006.01)
(Continued)

(52) U.S. Cl.
CPC ............. *A61B 6/541* (2013.01); *A61B 6/037* (2013.01); *A61B 6/5288* (2013.01); *A61B 8/5276* (2013.01); *A61B 5/02755* (2013.01); *A61B 5/7289* (2013.01); *A61B 8/543* (2013.01)

(58) Field of Classification Search
CPC .... A61B 6/037; A61B 6/541; A61B 8/5276; A61B 6/5288; A61B 5/02755; A61B 5/7289; A61B 8/543
See application file for complete search history.

(56) References Cited

U.S. PATENT DOCUMENTS 4,245,646 A    1/1981   Ionnou et al.
4,585,008 A *   4/1986   Jarkewicz ..................... 600/431
(Continued)

FOREIGN PATENT DOCUMENTS

DE          1015155      9/1957
JP          01299489 A    12/1989
(Continued)

OTHER PUBLICATIONS

Fulton et al., Event-by-event motion compensation in 3D PET, Nuclear Science Symposium Conference Record, 2003 IEEE, Issue Date: Oct. 19-25, 2003, p. 3286-3289.*
(Continued)

*Primary Examiner* — Bo J Peng

(57) ABSTRACT

In a diagnostic imaging system (10), a monitor (50) monitors periodic biological cycles of the subject (14). A trigger point detector (60) detects a time (t1, t2, . . . , tn) of a common, reoccurring reference point (R1, R2, . . . , Rn) in each periodic cycle of the subject (14). A sequence selector (62) selects a sequence (64) of nominal sampling segments (Si, S2, . . . , Sn). An adjustor (70) adjusts duration of each nominal sampling segment (Si, S2, . . . , Sn) to coincide with the times of detected reference points (R1, R2, . . . , Rn). A scaling processor (72) scales each adjusted segment based on a difference in duration between the corresponding nominal (Si, S2, . . . , Sn) and adjusted sampling segments (S'i, S'2, . . . , S'n).

14 Claims, 2 Drawing Sheets

(51) Int. Cl.
    *A61B 8/08*         (2006.01)
    *A61B 5/0275*     (2006.01)
    *A61B 5/00*         (2006.01)
    *A61B 8/00*         (2006.01)

(56) References Cited

U.S. PATENT DOCUMENTS

| | | | |
|---|---|---|---|
| 4,611,340 A | | 9/1986 | Okazaki |
| 4,865,043 A | * | 9/1989 | Shimoni ................. 600/513 |
| 5,431,161 A | * | 7/1995 | Ryals et al. ............. 600/425 |
| 5,800,355 A | | 9/1998 | Hasegawa |
| 6,294,788 B1 | | 9/2001 | Cooke et al. |
| 6,462,341 B1 | * | 10/2002 | Muehllehner ............ 250/363.03 |
| 6,507,752 B1 | | 1/2003 | Maeda |
| 6,690,965 B1 | | 2/2004 | Riaziat et al. |
| 2002/0163994 A1 | * | 11/2002 | Jones ............................. 378/21 |
| 2003/0016782 A1 | | 1/2003 | Kaufman et al. |
| 2003/0128801 A1 | | 7/2003 | Eisenberg et al. |
| 2003/0161440 A1 | | 8/2003 | Boyd et al. |
| 2004/0116804 A1 | | 6/2004 | Mostafavi |

FOREIGN PATENT DOCUMENTS

| | | |
|---|---|---|
| JP | 4270983 A | 9/1992 |
| WO | 2004078042 A1 | 9/2004 |

OTHER PUBLICATIONS

Huesman, R. H., et al.; List-Mode Maximum-Liklihood Reconstruction Applied to Positron Emission Mammography (PEM) with Irregular Sampling; 2000; IEEE Trans. on Medical Imaging; 19(5)532-537.

Jones, W. F.; Real-Time Event Stream Correction for Patient Motion in Clinical 3-D PET; 2002; IEEE; pp. 2062-2064.

Qi, J., et al.; List Mode Reconstruction for PET with Motion Compensation: A Simulation Study.

Mullani, N., et al.; Sensitivity Improvement of TOFPET by the Utilization of the Inter-Slice Coincidences; 1982; IEEE Trans. on Nuclear Science USA; ns-29(1)479-483.

\* cited by examiner

ECG-GATED TEMPORAL SAMPLING IN CARDIAC KINETIC MODELING

CROSS REFERENCE TO RELATED APPLICATIONS

This application claims the benefit of U.S. provisional application Ser. No. 60/675,187 filed Apr. 27, 2005, which is incorporated herein by reference.

The present invention relates to the diagnostic imaging arts. It finds particular application in conjunction with the Positron Emission Tomography (PET) kinetic imaging and will be described with particular reference thereto. However, it is to be appreciated that the present invention is applicable to SPECT, magnetic resonance imaging systems, computed tomography imaging systems, ultrasound and the like for a variety of imaging applications.

Kinetic imaging refers to the measurement of tracer uptake over time. The PET provides the tissue tracer concentration measurement required by the tracer kinetic model, with the final result being an image of the anatomic distribution of the biological process under study. The "tracer kinetic assay" method utilizes a radiolabeled, biologically active compound (tracer), and a mathematical model that describes the kinetics of the radiolabeled tracer to describe the distribution of the tracer in the body. Radiolabeled tracers and the tracer kinetic method are employed throughout the biological sciences to measure numerous biologic processes such as blood flow; membrane transport; metabolism; drug interactions with chemical systems; marker assays using recombinant DNA techniques; and the like.

The kinetic imaging is highly desirable in dynamic studies of the moving anatomical organs such as heart. One technique to collect dynamic diagnostic images is by using a dynamic imaging technique. In dynamic imaging, data acquisition continues over several successive temporal intervals, typically 3-20 seconds each, but potentially covering a much larger time range. The image from each temporal interval is displayed in a ciné fashion to show the time evolution of the radiopharmaceutical in the region of interest. One difficulty with dynamic imaging is that the images collected over relatively long imaging periods can be degraded by patient motion. Another problem with dynamic imaging, particularly over relatively short periods, is that the temporal period may span a fraction of a cardiac or other cycle, e.g., the image may be an integration over 3.5 cardiac cycles. Differences in the fraction of the cardiac cycle which contributes to the image can cause differences in the final image.

Another technique is gated imaging, such as cardiac gated imaging. In cardiac gated imaging, a characteristic point in each cardiac cycle triggers the collection of data. This enables the acquired data to be sorted by cardiac phase. More specifically, after the triggering time, the interval until the next triggering time is divided up into several equal segments, e.g. 16 segments per cardiac cycle. Over several cardiac cycles, complete data sets are acquired for each of the plurality of cardiac phases. Data from the same segment in each of a plurality of cycles is combined and averaged based on one of the known algorithms. However, the images, which are averaged over time, do not accurately show the dynamic change in the images versus time.

The present application contemplates a new and improved method and apparatus which overcomes the above-referenced problems and others.

In accordance with one aspect of the present invention, an apparatus for diagnostic imaging is disclosed. A monitor monitors periodic biological cycles of the subject. A trigger point detector detects a time of a common, reoccurring reference point in each periodic cycle of the subject. A sequence selector selects a sequence of nominal sampling segments, each nominal sampling segment having a start time and an end time. A synchronizing processor synchronizes the start and stop times of each nominal sampling segment with the times of detected reference points so that each sampling segment contains an integral number of biological cycles.

In accordance with another aspect of the present invention, a method of diagnostic imaging is disclosed. Radiation counts from a region of interest of a subject are detected. Periodic biological cycles of the subject are monitored. A reference point in each periodic cycle of the subject is detected. A sequence of nominal sampling segments is selected, each nominal sampling segment having a start time and an end time. The start and stop times of each nominal sampling segment are synchronized with the detected reference points so that each sampling segment contains an integral number of biological cycles.

In accordance with another aspect, an apparatus for dynamically imaging a region of interest of a subject is disclosed. A first mechanism detects at least one biological cycle of the subject. A second mechanism detects radiation counts emanating from the subject. A processor divides said radiation counts emanating from the subject into a predetermined number of sampling segments, each sampling segment comprising an integer number of biological cycles detected from said first mechanism.

In accordance with another aspect, the time, which takes an equal number of biological cycles to occur in each of the nominal sampling periods, is monitored. The image is normalized and reconstructed in accordance to this time.

One advantage of the present invention resides in improved image resolution of moving anatomy.

Another advantage resides in more accurate representation of dynamic changes in moving anatomy over time.

Another advantage resides in diagnostically improved dynamic imaging studies.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
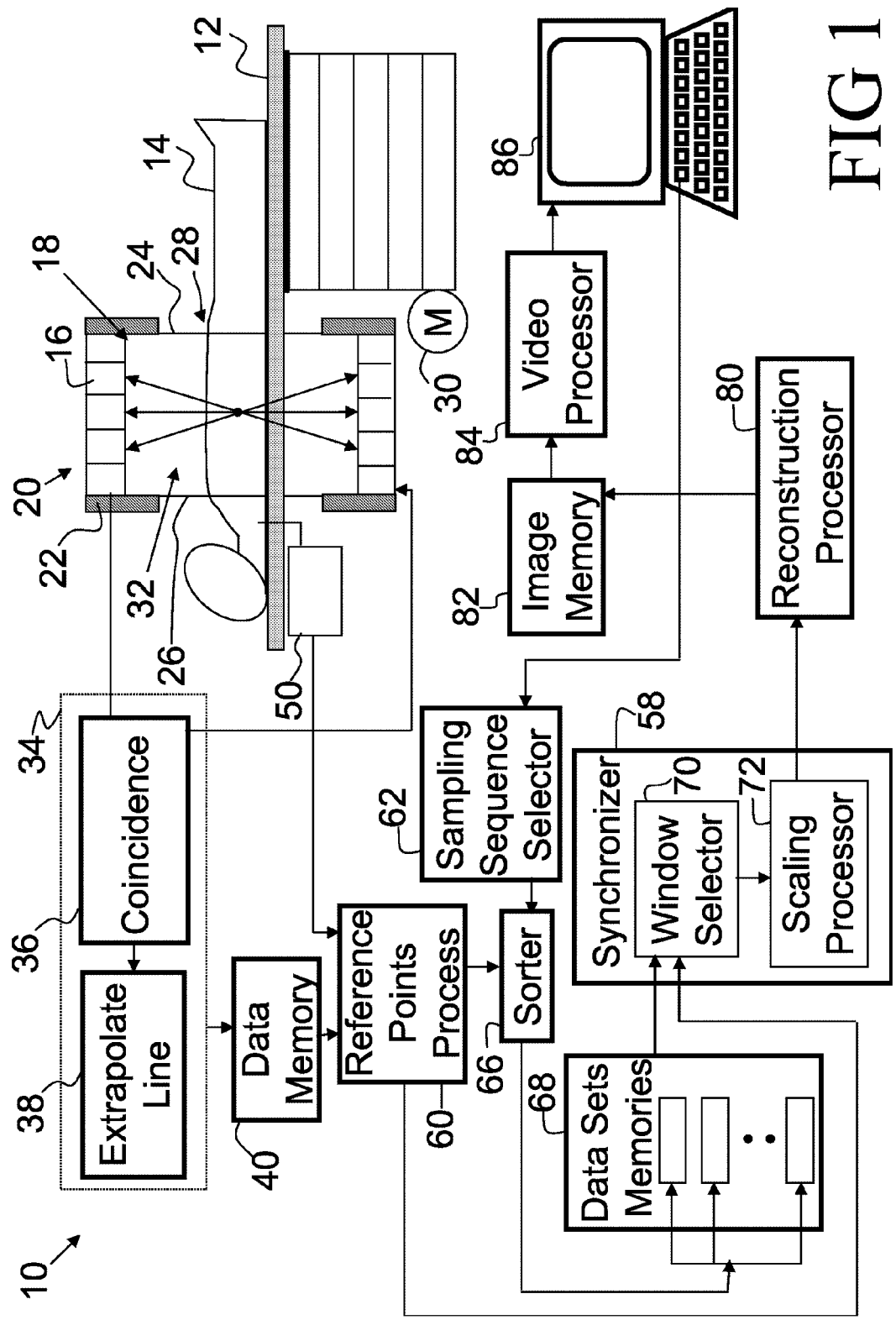
FIG. 1 is a diagrammatic illustration of a diagnostic imaging system.

With reference to FIG. 1, an imaging system 10 includes a subject support means 12, such as a table or couch, which supports a subject 14 being imaged. The subject 14 is injected with one or more radioisotopes or tracers to induce positron emission. A circularly cylindrical, annular array of detectors 16 is arranged around a bore 18 of a PET scanner gantry 20 that defines an axial field-of-view. When the detectors have planar faces, the detector array 16 may be an octagon or other regular polygon that approximates a circle. The detector elements are preferably mounted in sub-arrays that are mounted end-to-end to define the detector array 16. Radiation end shields 22 are mounted at an entrance 24 and an exit 26 of the circular bore 18 to define a receiving area or entrance aperture 28 of the PET scanner 20.

A drive 30, such as a motor, advances and/or retracts the subject support 12 to achieve the desired positioning of the subject 14 within an examination region 32 defined by the bore 18, e.g. with the region of interest centered in the field of view (FOV) of the detector array. Concurrent radiation event pairs detected by detectors 16 are identified by a line of response (LOR) calculating circuit or computer process 34. The LOR calculator 34 includes a coincidence detector 36 that determines when two events are within a preselected temporal window of being simultaneous. From the position of the detectors 16 and the position within each detector, at which the coincident radiation was received, a ray or line of response between the radiation detection points is calculated by a line extrapolator 38.

With continuing reference to FIG. 1, the LORs are saved in a data memory or buffer 40 preferably in a list mode, e.g. each LOR has a time stamp affixed to it. Such data storage mode allows retroactive manipulation on data. It is also contemplated that the attenuation data can be stored in a non list format. In this case, the collected events are stored in a sequential order to allow a retroactive manipulation on data.

A cycle monitor 50 monitors prespecified biological cycles of the patient 14. In one embodiment, the cycle monitor 50 monitors the patient's heart. More specifically, via leads attached to the patient 14, an ECG monitor acquires ECG data from the patient 14. Alternately, the heart may be monitored via another device such as, e.g., an echo heart monitor, an ultra-sound heart monitor, a heart sound monitor, a pulse oximeter, etc. In another embodiment, the cycle monitor 50 monitors patient's respiratory cycle. More specifically, a respiratory sensing belt is connected with a balanced bridge type pressure transducer which produces an electrical signal that varies in amplitude with the respiratory cycle. Commonly, the cardiac cycle is from about a half of a second to about one second in length and the respiratory cycle is from about five to about ten seconds in length.

Figure 2:
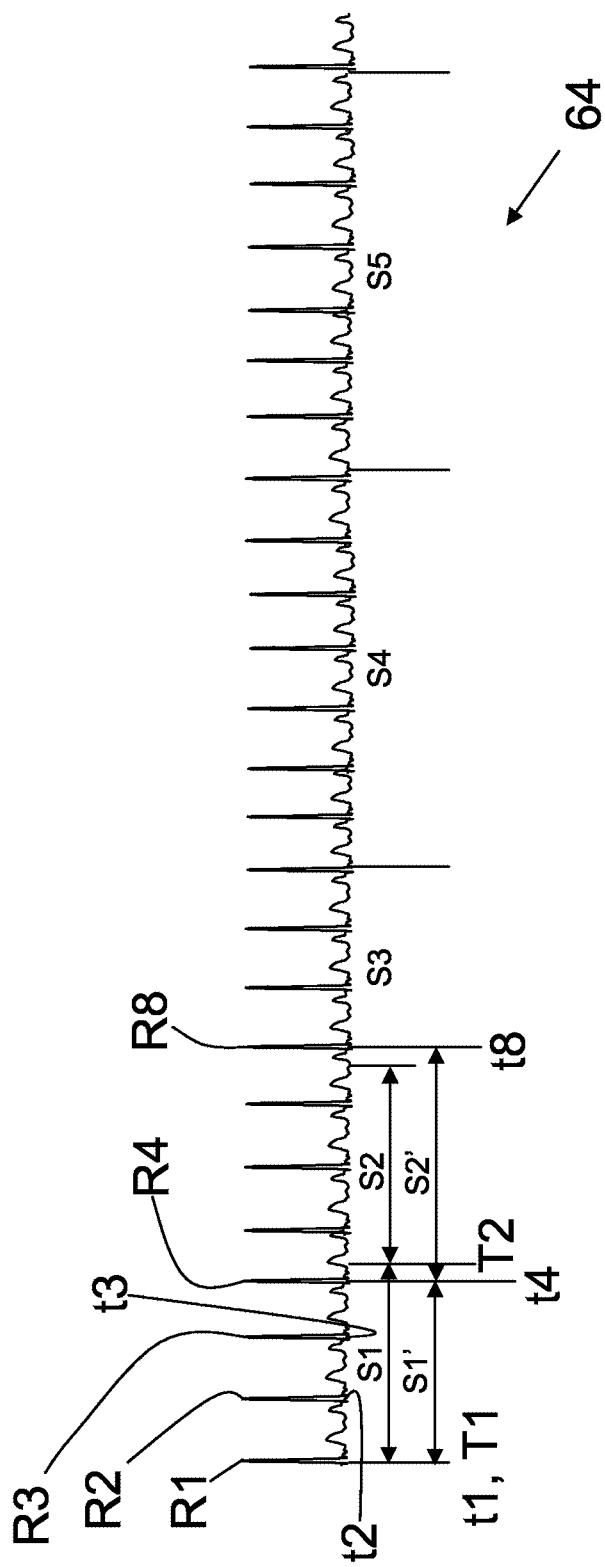
FIG. 2 is a diagrammatic illustration of the timing of data acquisition relative to a cardiac cycle.

With continuing reference to FIG. 1 and further reference to FIG. 2, a synchronizer circuit or computer process 58 synchronizes nominal sampling segments $S_1, S_2, \ldots, S_n$ with physiological gating such that each synchronized or modified sampling segment $S'_1, S'_2, \ldots, S'_n$ includes an integer number of cycles, e.g. heartbeats. More specifically, a reference point means or process 60 receives the information from the cycle monitor 50 and determines a reference or trigger point in the cycle, such as R peak of the patient's cardiac cycle at the end of the diastole phase. In cardiac studies, the cycle time is typically measured as the time from one R wave peak to the next R wave peak. For example, a first time t1 corresponds to a trigger point or peak R1 in a first cycle. A second time t2 corresponds to a second trigger point or peak R2, an end of the first cycle and a start of a second cycle. A third time t3 corresponds to a third trigger point or peak R3, an end of the second cycle and a start of a third cycle. The subsequent cycles are monitored in a similar manner, e.g. the cycle starts at the leading edge of the current trigger and ends at the leading edge of the next trigger. The cycle time is equal a time difference between times of the next and current triggers.

It is also contemplated that an alternative reference point in the cycle may be chosen. In this case, the cycle time is equal to a time difference between times of two reference points.

With continuing reference to FIGS. 1 and 2, a sampling sequence selector or process or means 62 determines a sampling scheme or sequence 64. In one embodiment, a user specifies the sampling sequence 64 which includes nominal sampling segments $S_1, S_2, \ldots, S_n$. For example, the acquired data can be split into the temporal sequence 64 which includes temporal intervals or sampling segments $S_1, S_2, S_3, S_4, S_5$ which each correspondingly equal to 3 sec, 3 sec, 3 sec, 5 sec, 5 sec, . . . , etc. In one embodiment, the sampling intervals $S_1, S_2, \ldots, S_n$ are specified as a number of heartbeats (HB), such as 3HB, 3HB, 3HB, 6HB, 6HB, 10HB, 10HB, etc. As yet another example, the cardiac cycle can be split into sampling segments $S_1, S_2, \ldots, S_n$, e.g. 8 or 16 sampling segments per each R-R interval. Of course, it is contemplated that the sampling segments might be arranged in any other appropriate temporal, heartbeat, or other sequences.

A sorter 66 sorts the LOR data into data sets collected during each of the sampling segments. More specifically, the sorter 66 sorts the attenuation data to substantially match each data collection start and end time T1, T2, . . . , Tn with the detected reference points R1, R2, . . . , Rn which occur substantially close in time to a start time T1, T2, . . . , Tn and an end time T2, T3, . . . , T(n+1) of each nominal sampling segment $S_1, S_2, \ldots, S_n$. For example, start and end times T1, T2 of the sampling segment $S_1$ are matched with first and fourth trigger times t1, t4 and consequently with the detected reference points R1, R4 which occur substantially close in time to the start and end times T1, T2. The sorted and correlated LOR data is stored in a data sets memories or lookup table 68.

A window selector or selecting means or processor 70 modifies each sampling segment $S_1, S_2, \ldots, S_n$ such that each sampling segment includes an integer number of cardiac cycles or heartbeats. More specifically, the window selector 70 dynamically increases or decreases each sampling segment $S_1, S_2, \ldots, S_n$ in accordance with the timing of the closest detected reference or trigger points. For example, the overall time of the first sampling segment $S_1$ is decreased such that the nominal stop time T2 of the first sampling segment $S_1$ is shifted to a fourth time t4, corresponding to the closest detected reference or trigger point R4. Likewise, the nominal start and stop times T2, T3 of the second sampling segment S2 are adjusted to coincide respectively with the closest reference or trigger points R4, R8. Thus, the temporal sequence 64 becomes a modified sequence 64' which includes modified sampling segments $S'_1, S'_2, \ldots, S'_1$ which each respectively equal to an integer number of cycles, for example, to about 2.9 sec, 3.1 sec, 2.9 sec, 5.1 sec, 5.0 sec, . . . , etc. The exact duration of each modified sampling segment $S'_1, S'_2, \ldots, S'_n$ is defined retrospectively from the data sets stored in the list mode. In this manner, the window selector 70 assures that each temporal sample includes the same fraction of the diastolic phase as the other samples which prevent creating bias in the distribution of the radioisotope.

Segments of nominally the same duration are in fact shorter or longer. Shortened segments have a proportionately smaller number of LORs and lengthened segments have a proportionately higher number. A scaling processor or means 72 multiplies the LOR count along each trajectory by an appropriate scaling factor in accordance with the deviation of the modified or actual segment time relative to the predefined time of the corresponding nominal segment. Alternatively, the image can be reconstructed with non-weighted LOR counts and the reconstructed image weighted instead.

A data reconstruction processor or process 80 reconstructs an electronic image representation of the subject 14 from the weighed LORs. The resultant image representation is stored in an image memory 82. Portions of the stored image representation are retrieved by a video processor 84 and converted to an appropriate format for display on a monitor 86, such as a video, CCD, active matrix, plasma, or other monitor. Of course, a color printer or other output device may also be used to present the data in a convenient format.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

The invention claimed is:

1. An apparatus for detecting radiation counts from a region of interest of a subject, the apparatus comprising:
   a plurality of radiation detectors which acquire the radiation counts;
   a monitor which monitors periodic biological cycles of the subject;
   a trigger point detector which detects a time of a common reference point in each of the monitored periodic biological cycles of the subject;
   a sequence selector which selects a sequence of nominal sampling segments, each nominal segment spanning a plurality of the periodic biological cycles, each nominal sampling segment having a selected duration, a start time and an end time; and
   one or more processors programmed to:
      synchronize the start time of each nominal sampling segment with the detected reference point in a first of the periodic biological cycles and the stop time with the detected reference point in a subsequent one of the periodic biological cycles.

2. The apparatus as set forth in claim 1, wherein the one or more processors are further programmed to:
   sort the acquired radiation counts collected during each nominal segment based on a proximity of each acquired radiation count to the detected reference points into data sets, such that each data set corresponds to a corresponding common physiological cycle phase.

3. The apparatus as set forth in claim 1, wherein the one or more processors are further programmed to:
   adjust the selected duration of each nominal sampling segment such that the start times and end times coincide with the closest detected reference points.

4. The apparatus as set forth in claim 3, wherein the one or more processors are further programmed to:
   scale a number of radiation counts recorded in each duration adjusted sampling segment in accordance with a deviation between the adjusted duration of the adjusted sampling segment and the preselected duration of the nominal sampling segment.

5. The apparatus as set forth in claim 3, further including:
   a PET gantry which receives the subject injected with a radiopharmaceutical, the gantry includes the plurality of radiation detectors around the subject;
   a coincidence detector for detecting substantially pairs of coincidently detected radiation events;
   a line of response determining process for determining a line of response between each pair of substantially coincidently detected radiation events; and
   the one or more processors are programmed to reconstruct the lines of response from each segment into an image representation.

6. The apparatus as set forth in claim 5, wherein the one or more processors are programmed to:
   scale one of the lines of response and the image representation.

7. The apparatus as set forth in claim 6, wherein the processor is further programmed to:
   scale the number of the lines of response in each segment in accordance with the difference between the adjusted duration of each segment and the preselected duration of the corresponding nominal segment.

8. The apparatus as set forth in claim 1, wherein each nominal sampling segment is a plural integer multiple of the periodic biological cycles.

9. An apparatus for detecting radiation counts from a region of interest of a subject, the apparatus comprising:
   a plurality of radiation detectors which acquire radiation counts;
   a monitor which monitors periodic biological cycles of the subject;
   a trigger point detector which detects a time of a common reference point in each periodic cycle of the subject;
   a sequence selector which selects a sequence of nominal sampling segments, each nominal sampling segment having a start time and an end time; and
   a synchronizing processor which synchronizes the start and stop times of each nominal sampling segment with the times of detected reference points, the synchronizing processor further including:
      an adjustor for adjusting a duration of each nominal sampling segment such that the start times and the end times coincide with the closest detected reference points, and
      a scaling processor for scaling each adjusted sampling segment based on a difference in duration between the corresponding nominal and adjusted sampling segments.

10. A method of diagnostic imaging comprising:
   detecting radiation counts from a region of interest of a subject over a plurality of periodic biological cycles;
   monitoring periodic biological cycles of the subject;
   detecting a common reference point in each periodic cycle of the subject;
   selecting a sequence of nominal sampling segments spanning a non-integer plural number of the periodic biological cycles, each nominal sampling segment having a start time and an end time;
   synchronizing the start and stop times of each nominal sampling segment with the detected reference points such that the start and end times of each nominal sampling segment are temporarily shifted to coincide with the closest detected reference points, the synchronizing including:
      scaling each adjusted sampling segment based on a difference between the corresponding nominal and adjusted sampling segments.

11. The method as set forth in claim 10, wherein the scaling includes adjusting a number of radiation counts in each adjusted segment in accordance with a temporal difference between durations of each adjusted and nominal sampling segment.

12. The method as set forth in claim 10, further including:
   reconstructing the radiation counts of each adjusted segment into an image representation.

13. The method as set forth in claim 12, wherein the scaling includes scaling each image representation in accordance with a difference between the durations of each adjusted sampling segment and the nominal sampling segment.

14. An apparatus for dynamically imaging a region of interest of a subject the apparatus comprising:
   a first mechanism which detects at least one biological cycle of the subject;
   a second mechanism which detects radiation counts emanating from the subject; and
   a processor that divides said radiation counts emanating from the subject into a plurality of sampling segments, each sampling segment comprising a plural integer number of biological cycles detected from said first mechanism;
   wherein said processor scales a number of radiation counts detected in each sampling segment in accordance with relative time durations of the sampling segments.

* * * * *